United States Patent

Sugihara et al.

Patent Number: 6,034,520
Date of Patent: Mar. 7, 2000

[54] METHOD OF DETERMINATION OF ACTIVE IONS BY ELECTRIC CONDUCTIVITY AND ELECTRIC CONDUCTIVITY METERING SYSTEM THEREFOR

[75] Inventors: Toshio Sugihara; Mitsuo Suzuki; Marcos Masaki Komiya, all of Tokyo-to, Japan

[73] Assignee: Life Energy Industry Inc., Japan

[21] Appl. No.: 08/845,357

[22] Filed: Apr. 24, 1997

Related U.S. Application Data

[63] Continuation-in-part of application No. 08/678,061, Jul. 9, 1996, Pat. No. 5,787,525.

[51] Int. Cl.[7] ................................................ G01N 27/06
[52] U.S. Cl. .......................... 324/71.1; 324/439; 324/441; 324/450; 324/717
[58] Field of Search .................... 324/439, 441, 324/444, 450, 464, 713, 717, 722, 724, 71.1

[56] References Cited

U.S. PATENT DOCUMENTS

| | | | |
|---|---|---|---|
| 4,871,427 | 10/1989 | Kolesar, Jr. | 324/439 |
| 5,218,312 | 6/1993 | Moro | 324/444 |
| 5,289,132 | 2/1994 | Oksman et al. | 324/713 |
| 5,517,181 | 5/1996 | Gray et al. | 340/605 |
| 5,521,510 | 5/1996 | Schunck et al. | 324/439 |

*Primary Examiner*—Diep N. Do
*Attorney, Agent, or Firm*—Wenderoth, Lind & Ponack, L.L.P.

[57] ABSTRACT

Provided is a method and metering system for the determination of active ions emitted from certain active substances such as rayon fibers containing fine particles of tourmaline known to exhibit permanent spontaneous polarization. The method comprises: continuously bringing air free from carbon dioxide as a carrier gas into contact with a bed of the active ion-emitting source material to carry off the active ions emitted therefrom; introducing the air after contact with the source material into distilled water; and measuring increase in the electric conductivity of the distilled water caused by the absorption of the active ions from the flow of the air as a carrier gas. The metering system comprises: a feed source of the non-ionic inert gas; a sample holder to contain the source material emitting active ions; a vessel containing distilled water to receive the air carrying the active ions; a means to determine the electric conductivity of the water; and pipelines connecting these parts for the flow of air.

9 Claims, 2 Drawing Sheets

METHOD OF DETERMINATION OF ACTIVE IONS BY ELECTRIC CONDUCTIVITY AND ELECTRIC CONDUCTIVITY METERING SYSTEM THEREFOR

This is a continuation-in-part application from a copending U.S. patent application Ser. No. 08/678,061 filed Jul. 9, 1996, U.S. Pat. No. 5,787,525.

BACKGROUND OF THE INVENTION

The present invention relates to a method for the determination of active ions and a metering system therefor. More particularly, the present invention relates to a method for the determination method of active ions, which cannot be detected in the prior art due to lack of a suitable means therefor, as well as to a metering system for the determination of active ions.

The active ion here implied is a kind of negative ions capable of exhibiting an invigorating effect on the living body by normalizing the autonomic nervous system or motorial nervous system. As a consequence, the person under the influence of active ions is imparted with beneficial effects such as sleep-stimulation, ataraxy, recovery promotion from fatigue and so on.

The active ions, however, can hardly be detected by using a conventional voltameter because the quantity thereof is extremely small. A special metering instrument is proposed heretofore for the detection of an extremely small quantity of electric charges, by which the electric charges on the dust particles floating in the air can be quantitatively determined. The active ions, however, cannot be detected even by the use of such a sensitive instrument because the quantity thereof is too small to be detected thereby. Accordingly, absolutely no means is known in the prior art for the detection of active ions and quantitative estimation of the quantity thereof.

SUMMARY OF THE INVENTION

The present invention accordingly has an object to provide a simple and convenient means, i.e. method and metering system, for the detection and quantitative determination of active ions of which no effective means is known in the prior art for the detection and quantitative determination notwithstanding the widely recognized beneficial physiological effects thereof on the living body.

Namely, the inventors have conducted extensive investigations with an object to develop a method for the detection and quantitative determination of active ions and, as a consequence, have arrived at a discovery that the active ions can be, though indirectly, detected and quantitatively determined when a non-ionic inert carrier gas carrying the active ions is brought into contact with distilled water of which the electric conductivity is measured to estimate the increase in the conductivity caused by the active ions.

Thus, the method of the present invention for the determination of active ions comprises the steps of:

(a) bringing a non-ionic inert gas continuously into contact with an emitting source of active ions so as to carry off the active ions with the gas;

(b) bringing the inert gas carrying the active ions into contact with distilled water; and (c) measuring the electric conductivity of the distilled water after contact with the inert gas carrying the active ions.

The metering system of the present invention for the determination of active ions comprises:

(A) a feed source of a non-ionic inert gas;

(B) an elongated vertically installed cylindrical vessel equipped with a temperature-detecting means and a heating means and having an inlet port for the non-ionic inert gas at one end and an outlet port for the gas at the other end opposite to the inlet port, which holds a source material emitting active ions in the middle part thereof;

(C) a vessel containing distilled water having a thermostat means;

(D) a first pipeline connecting the inlet port of the elongated vessel (B) to the feed source of the non-ionic inert gas (A);

(E) a second pipeline connecting the outlet port of the elongated vessel (B) to the vessel (C) containing distilled water; and (F) an instrument for the determination of the electric conductivity of the distilled water contained in the vessel (C) with electrodes kept in the distilled water.

Optionally, a means for removal of ionic material is provided in the middle way of the first pipeline (D) connecting the inlet port of the elongated vessel (B) to the feed source of the non-ionic inert gas (A).

DETAILED DESCRIPTION OF THE PREFERRED EMBODIMENTS

Figure 1:
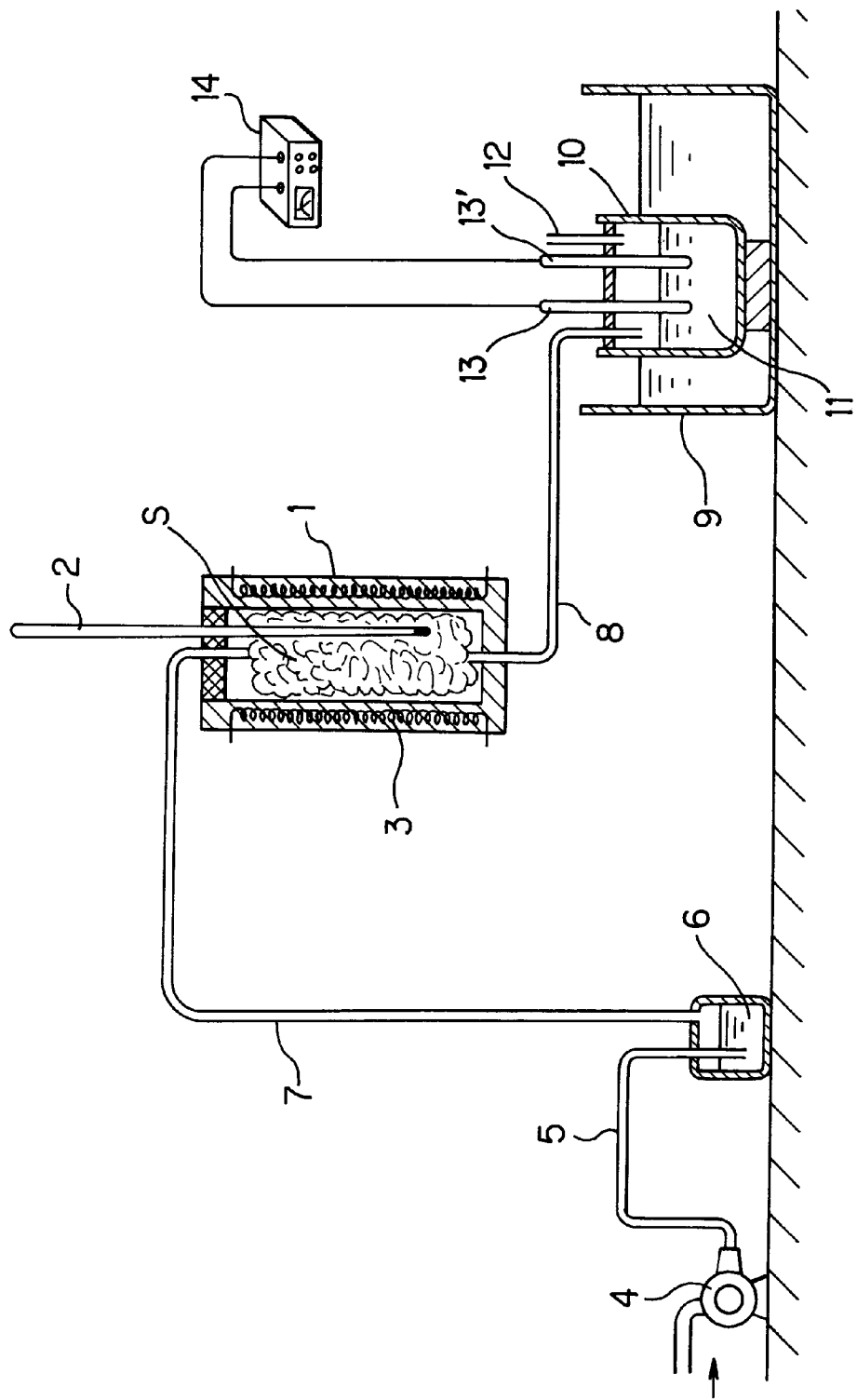
FIG. 1 is a schematic illustration of the metering system for the detection and determination of active ions according to the invention.

In the following, the present invention is described in detail by making reference to the accompanying drawing. FIG. 1 schematically illustrates an example of the assembly of the inventive metering system for the detection and quantitative determination of active ions emitted from a source material. A sample-holder vessel 1 is filled with the source material S emitting active ions. The sample holder 1 is an elongated cylindrical vessel made from heat-resistant glass and installed usually in a vertical disposition. The sample holder 1 is filled at least partly in the middle portion thereof with the active ion-emitting sample S. If necessary, the bed of the sample material S is sandwiched with a gas-permeable sheets (not shown in the figure) such as filter paper at the top and at the bottom so as to prevent movement and scattering of the sample material S. The sample holder vessel 1 is equipped with a temperature detecting means such as a thermometer 2 and a heating means such as an electric resistance heater 3 in such a way that the temperature of the sample material S can be controlled at a desired temperature.

When detection or determination of active ions is performed, a non-ionic inert gas held in a gas cylinder 4 is introduced through the pipeline 5 into a decarbonater 6 to remove the carbon dioxide contained therein and the thus decarbonated inert gas is introduced, through the pipeline 7, to the inlet port of the sample holder 1 at the top thereof. The active ions emitted from the sample S are carried off by the inert gas as the carrier flowing in contact with the sample S.

The inert gas carrying the active ions is discharged out of the outlet port at the bottom of the sample holder 1 and sent through the pipeline 8 to the vessel 10 containing distilled water 11 to be finally purged to the open air through the outlet 12 after being blown at the surface of the distilled water 11. Thus, the active ions carried by the inert gas are taken into the distilled water 11 so that the electric conductivity of the distilled water is gradually increased as the time of blowing the active ion-carrying inert gas is increased. The distilled water 11 in the vessel 10 is kept at a specified temperature by means of the thermostat 9. A pair of electrodes 13, 13' immersed in the distilled water 11 are connected to a meter 14 for the measurement of the electric conductivity.

It is important that the vessel 10 for containing the distilled water 11 is made from a material free from any factors which may affect the electric conductivity of the distilled water 11, for example, by certain ionic species leached out from the vessel wall into the distilled water. In this regard, conventional glass materials such as soda glass are not suitable due to possible leaching of alkali ions to cause a bias to the value of the electric conductivity determined in the meter 14 although correction for the bias can be undertaken by carrying out a blank test.

It is essential that the conductivity measurement of the distilled water 11 is performed at a constant temperature because the electric conductivity of water varies depending on the temperature. Though not particularly limitative, the conductivity measurement of the distilled water is performed usually at 22° C.

In carrying out the inventive method, the active ions emitted from the sample material S are carried off and transported by a non-ionic inert gas as a carrier gas. Since the quantity of the active ions emitted from the source material S is extremely small, it is very important in order to obtain accurate and reproducible results of the conductivity measurement that the carrier gas per se is absolutely free from active ions or free from any substances from which active ions could eventually be generated. Examples of suitable inert gases include nitrogen, oxygen, hydrogen, helium, neon and argon as well as mixtures thereof. A convenient way is to use air as the carrier gas if the carbon dioxide as an ionic substance can be completely removed therefrom in the decarbonator 6. Decarbonation of air can be performed by contacting the air with an aqueous solution of an organic amine compound such as triethanolamine, solids of alkali metal hydroxides such as potassium hydroxides, strongly anionic ion-exchange resins and the like.

The above described method and metering system of the invention can be applied to the determination of the active ions emitted from various kinds of active ion-emitting source materials, of which typical ones include certain natural minerals and ceramics emitting active ions as well as fibers and shaped plastic articles containing fine particles of such an active ion-emitting material. One of the typical minerals emitting active ions is tourmaline which is highlighted in recent years.

Tourmaline is a mineral having a chemical composition expressed by the formula $MX_3B_3Al_3 (AlSi_2O_9)_3 (O,OH,F)_4$, in which M is an atom of sodium or calcium and X is an atom of aluminum, iron, lithium, magnesium or manganese.

High-quality crystals of tourmaline, which may be naturally occurring or can be synthesized artificially, are known as a gem stone useful in a jewelry application. Tourmaline is also known as a unique mineral exhibiting spontaneous permanent electric polarization and the vector of polarization is unaffected by any external electric field. Besides the strongest permanent polarization among known minerals, tourmaline is known to emit far-infrared radiation. Further, tourmaline is a mineral to exhibit a piezoelectric effect, by which dielectric polarization is induced when an external stress is applied to the crystal, and a pyroelectric effect, by which electric charge is accumulated on the surface when a part of the crystal is heated.

The method and metering system of the invention are particularly suitable for the determination of active ions emitted from a fibrous material into which fine particles of a natural mineral or ceramic material emitting active ions, such as tourmaline mentioned above, are incorporated.

Examples of the fibrous material, into which fine particles of an active ion-emitting substance are incorporated, include polyvinyl alcohol fibers and rayon fibers.

It has been discovered that presence of moisture has some influences on the efficiency of the carrying-off process of the active ions as emitted from an active ion-emitting substance by the non-ionic inert carrier gas. When tourmaline is the active substance, for example, the fibers incorporated with fine particles of tourmaline should preferably contain moisture in an amount not exceeding 1.5% by weight or, more preferably, from 0.3 to 0.9% by weight. When the moisture content in the fibrous material is too high, the active ions emitted from the active particles may be absorbed by the moisture in the fibrous material so that a negative error is caused in the value of the electric conductivity of the distilled water as measured. When the moisture content in the fibrous material is too low, a full efficiency of active ion emission from the active particles cannot be obtained. Further, assuming that the fibrous material containing fine tourmaline particles is used for a health commodity, it is preferable that the above described metering method of the active ions is conducted by keeping the fibrous material as the active ion source S kept at a temperature of 35 to 39° C. approximating the human body temperature.

The above mentioned moisture content is defined by the equation (moisture content, %)=$(W_1-W_2)/W_1 \times 100$, in which $W_1$ is the weight of the sample after full drying, for example, by heating at 40° C. for 1 to 2 hours but before the test and $W_2$ is the weight of the same sample after testing, for example, by passing the inert gas at 35° C. for 3 hours.

In the following, the method and the metering system of the invention for the determination of active ions are described in more detail by way of Examples, as preceded by a description of the preparation procedure for rayon fibers containing fine particles of tourmaline.

Sample Preparation 1

According to the conventional procedure, an alkali cellulose was prepared from 100 parts by weight of wood pulp which was agitated at room temperature for 2 hours with addition of 350 parts by weight of a 20% by weight aqueous solution of sodium hydroxide. The alkali cellulose was admixed with 30 parts by weight of carbon disulfide and agitated at room temperature for 3 hours to give a solution of a sodium cellulose xanthate.

In the next place, the above prepared xanthate solution was diluted by the addition of an aqueous solution of sodium hydroxide to give a spinning solution containing 8.7% by weight of cellulose, 6.0% by weight of total alkali and 2.4% by weight of total sulfur. The spinning solution was admixed with fine particles of tourmaline having a particle diameter not exceeding 0.2 μm and an average particle diameter of 0.15 μm obtained by the method of water-granulation in an amount of 1.0% by weight based on the cellulose content.

The spinning solution containing tourmaline particles was subjected to spinning into a spinning bath at 50° C. containing 120 g/liter of sulfuric acid, 280 g/liter of sodium sulfate and 15 g/liter of zinc sulfate at a spinning velocity of 60 meters/minutes through a spinnerette having 50 holes of 0.08 mm diameter followed by stretching in a conventional two-bath stretch spinning method to give rayon fibers of 15 denier fineness containing tourmaline particles.

Sample Preparation 2

The procedure for the preparation of rayon fibers containing tourmaline particles was substantially the same as in Sample Preparation 1 described above excepting for the replacement of the tourmaline particle having a particle diameter not exceeding 0.2 μm with the same amount of tourmaline particles having a particle diameter not exceeding 1.0 μm and an average particle diameter of 0.8μm.

EXAMPLE 1

The sample holder 1 made from heat-resistant glass of the active ion metering system illustrated in FIG. 1 was filled with 20 g of the tourmaline-containing rayon fibers prepared in Sample Preparation 1 as disintegrated into loose lumps to form a bed S of rayon fibers which contained 1.2% by weight of moisture. While keeping the fiber bed S at a temperature of 37° C., air was introduced into the sample holder 1 to flow through the fiber bed S at a rate of 100 ml/minute after decarbonation by passing through a decarbonating bath of a 5% by weight aqueous solution of triethanolamine.

The air discharged out of the sample holder 1 at the bottom thereof after contacting with the tourmaline-containing rayon fibers was introduced into a 1-liter hard glass beaker 8 as the conductivity cell and contacted with 500 ml of distilled water contained therein at a temperature of 21.0±0.1° C. to be finally discharged out of the system.

Figure 2:
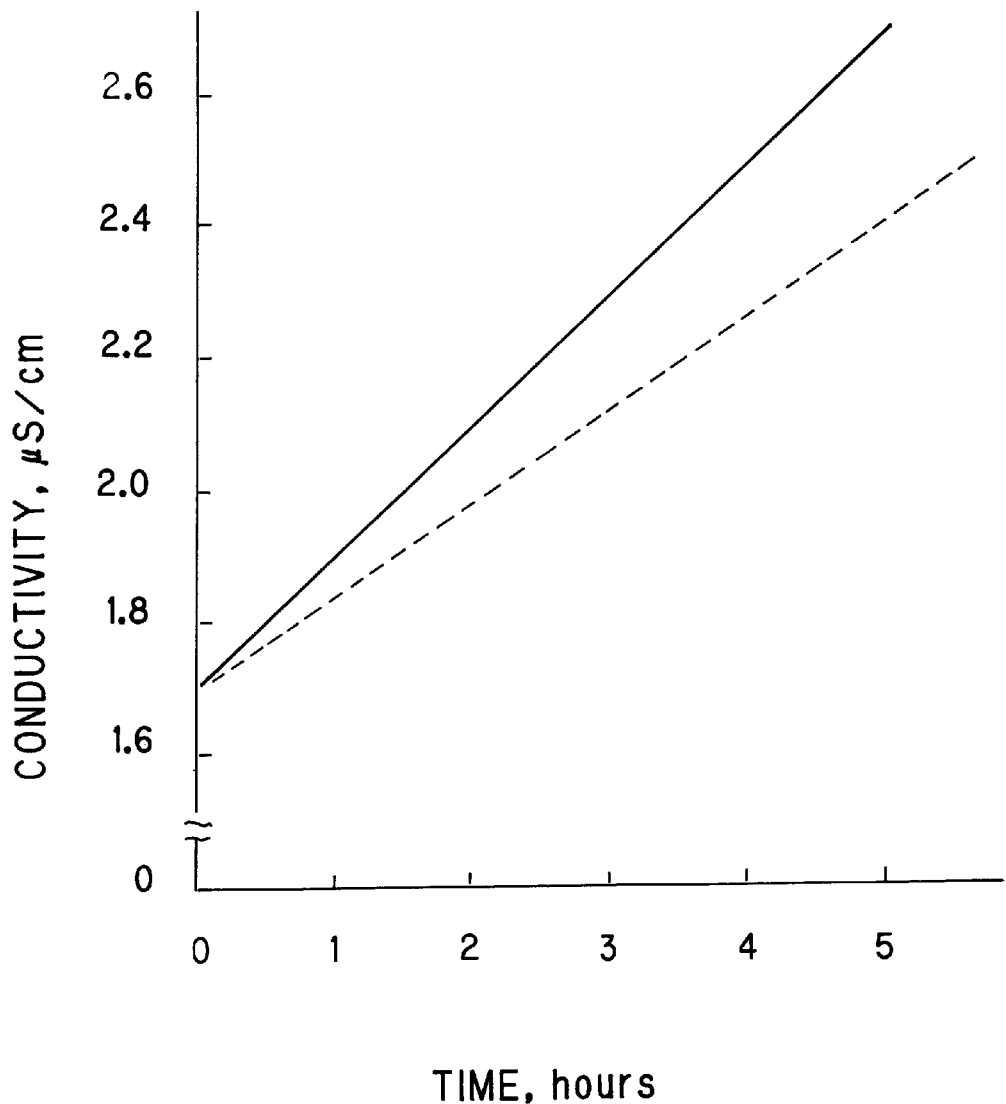
FIG. 2 is a graph showing electric conductivity of the distilled water as a function of the time for introduction of the inert gas carrying the active ions emitted from rayon fibers containing fine particles of tourmaline.

The electric conductivity of the water in the beaker was continuously determined and recorded by using a precision conductivity meter (Precision LCR Meter Model 4285A, manufactured by Hewlett Packard Co.) to give the results graphically shown by the solid line of FIG. 2 as a function of the contacting time of the air flow with the tourmaline-containing rayon fibers up to 5 hours.

Further, the same measurement as above was repeated excepting for the replacement of the tourmaline-containing rayon fibers prepared in Sample Preparation 1 with the rayon fibers prepared in Sample Preparation 2 to give the results shown by the broken line in FIG. 2.

As a control, the same measurement was performed excepting for the replacement of the tourmaline-containing rayon fibers with conventional rayon fibers containing no tourmaline particles to find that the electric conductivity of the water was 1.84 μS/cm after 3 hours of the contacting time.

EXAMPLE 2

Rayon fiber samples containing the tourmaline particles in a varied amount up to 7% by weight based on the rayon were prepared in substantially the same manner as in Sample Preparation 1 or 2 and the same conductivity measurement as in Example 1 was conducted with these rayon fiber samples to give the results shown in Table 1 which indicates the electric conductivity of the water after 3 hours of the contacting time for each sample of different tourmaline contents.

TABLE 1

| Conductivity of water, μS/cm | | |
|---|---|---|
| Content of tourmaline | Max. particle diameter of tourmaline | |
| particles, % by weight | 0.2 μm | 1.0 μm |
| 0.05 | 2.24 | 2.10 |
| 0.1 | 2.39 | 2.15 |
| 0.2 | 2.42 | 2.17 |
| 0.3 | 2.42 | 2.16 |
| 0.5 | 2.34 | 2.13 |
| 1.0 | 2.28 | 2.13 |
| 2.0 | 2.19 | 2.11 |
| 3.0 | 2.15 | 2.08 |
| 5.0 | 2.10 | 2.10 |
| 7.0 | 2.06 | 2.08 |

What is claimed is:

1. A method for the determination of active ions which comprises the steps of:
   (a) bringing a non-ionic inert gas continuously into contact with an emitting source of active ions in a first vessel so as to remove the active ions from the first vessel with the gas;
   (b) bringing the inert gas carrying the active ions into contact with the distilled water in a second vessel; and
   (c) measuring the electric conductivity of the distilled water after contact with the inert gas carrying the active ions so that the active ions interact with the water wherein the conductivity indicates the amount of active ions.

2. The method for the determination of active ions as claimed in claim 1 in which the non-ionic inert gas is air which is treated so that it is substantially free from carbon dioxide.

3. The method for the determination of active ions as claimed in claim 1 in which contacting of the non-ionic inert gas with the emitting source of active ions in step (a) is performed at a constant temperature.

4. The method for the determination of active ions as claimed in claim 3 in which the constant temperature is in the range from 35 to 39° C.

5. The method for the determination of active ions as claimed in claim 1 in which contacting of the non-ionic inert gas with the emitting source of active ions in step (a) is performed under a constant moisture content of the emitting source of active ions.

6. The method for the determination of active ions as claimed in claim 5 in which t he constant moisture content is does not exceed 1.5% by weight.

7. A metering system for the determination of active ions which comprises:
   (A) a feed source of a non-ionic inert gas;
   (B) an elongated vertically installed cylindrical vessel as a sample holder equipped with a temperature detector and a heater and having an inlet port for a non-ionic inert gas at one end and an outlet port for the gas at the other end opposite to the inlet port, which holds a source material emitting active ions contained therein;
   (C) a vessel containing distilled water having a thermostat;

(D) a first pipeline connecting the inlet port of the elongated vessel (B) to the feed source of the non-ionic inert gas (A);

(E) a second pipeline connecting the outlet port of the elongated vessel (B) to the vessel (C) containing distilled water and the outlet of said second pipeline proximate to the surface of the distilled water; and (F) an instrument comprising electrodes for the determination of the electric conductivity of the distilled water contained in the vessel (C) with said electrodes being kept in the distilled water.

8. The metering system for the determination of active ions as claimed in claim 7 which further comprises:

(G) a means for removal of ionic material from the non-ionic inert gas in the middle of the first pipeline (D) connecting the inlet port of the elongated vessel (B) to the feed source of the non-ionic inert gas (A).

9. The metering system for the determination of active ions as claimed in claim 7 in which the elongated vessel (B) is provided with a temperature controller.

* * * * *